(12) United States Patent
Takeshima

(10) Patent No.: US 12,271,441 B2
(45) Date of Patent: Apr. 8, 2025

(54) MEDICAL DATA PROCESSING APPARATUS AND METHOD

(71) Applicant: Canon Medical Systems Corporation, Otawara (JP)

(72) Inventor: Hidenori Takeshima, Kawasaki (JP)

(73) Assignee: Canon Medical Systems Corporation, Otawara (JP)

( * ) Notice: Subject to any disclaimer, the term of this patent is extended or adjusted under 35 U.S.C. 154(b) by 471 days.

(21) Appl. No.: 17/305,259

(22) Filed: Jul. 2, 2021

(65) Prior Publication Data

US 2022/0019850 A1     Jan. 20, 2022

(30) Foreign Application Priority Data

Jul. 15, 2020   (JP) ................................ 2020-121510

(51) Int. Cl.
*G06F 18/214* (2023.01)
*G06V 10/774* (2022.01)
*G06V 10/776* (2022.01)
*G16H 50/20* (2018.01)

(52) U.S. Cl.
CPC .......... *G06F 18/214* (2023.01); *G06V 10/774* (2022.01); *G06V 10/776* (2022.01); *G16H 50/20* (2018.01); *G06V 2201/03* (2022.01)

(58) Field of Classification Search
CPC .. G06F 18/214; G06V 10/774; G06V 10/776; G06V 2201/03; G16H 50/20; G16H 30/20; G16H 30/40; G16H 50/70
See application file for complete search history.

(56) References Cited

U.S. PATENT DOCUMENTS

| 11,830,585 | B2 * | 11/2023 | Golenski | G16H 40/67 |
| 11,862,339 | B2 * | 1/2024 | Wall | A61B 5/16 |
| 2015/0272448 | A1 * | 10/2015 | Fonte | A61B 5/0263 600/504 |
| 2016/0166209 | A1 * | 6/2016 | Itu | A61B 6/5217 600/408 |
| 2017/0337682 | A1 | 11/2017 | Liao et al. | |
| 2018/0018590 | A1 | 1/2018 | Szeto et al. | |
| 2019/0336033 | A1 | 11/2019 | Takeshima | |

(Continued)

FOREIGN PATENT DOCUMENTS

| JP | 2016-173682 A | 9/2016 |
| JP | 6545887 B2 | 7/2019 |

(Continued)

OTHER PUBLICATIONS

Japanese Office Action issued Nov. 7, 2023 in Japanese Application 2020-121510, 8 pages.

*Primary Examiner* — Lewis G West
(74) *Attorney, Agent, or Firm* — Oblon, McClelland, Maier & Neustadt, L.L.P.

(57) ABSTRACT

According to one embodiment, a medical data processing apparatus includes a processing circuitry. The processing circuitry is configured to: obtain first medical data; generate, based on the first medical data, a derived model from a trained model; obtain second medical data for a same subject as a subject of the first medical data and with an acquisition parameter different from an acquisition parameter of the first medical data; and apply the second medical data to the derived model to generate third medical data.

13 Claims, 9 Drawing Sheets

(56) References Cited

U.S. PATENT DOCUMENTS

| | | | | |
|---|---|---|---|---|
| 2019/0391920 A1* | 12/2019 | Gupta | ................... | G06N 20/00 |
| 2020/0003858 A1* | 1/2020 | Takeshima | ......... | G01R 33/5608 |
| 2020/0133761 A1* | 4/2020 | Paruthi | ............... | G06F 11/0751 |
| 2020/0365255 A1* | 11/2020 | Hayashitani | ........... | G16H 50/20 |
| 2020/0365269 A1* | 11/2020 | Kartoun | ................. | G16H 70/60 |
| 2020/0387430 A1* | 12/2020 | Hironaka | ............ | G06F 11/1469 |
| 2021/0026809 A1* | 1/2021 | Hsu | ....................... | G06F 16/144 |
| 2021/0052247 A1 | 2/2021 | Kobayashi | | |
| 2021/0150783 A1* | 5/2021 | Arberet | .................. | G06N 3/045 |
| 2021/0174500 A1* | 6/2021 | Van Pelt | ............... | G16H 50/50 |
| 2021/0241118 A1* | 8/2021 | Zarkov | .............. | G06F 16/2379 |
| 2021/0256615 A1* | 8/2021 | Hayward | ................. | G06N 3/08 |
| 2021/0265015 A1* | 8/2021 | Parnaby | ................ | G16B 40/10 |
| 2021/0295996 A1* | 9/2021 | Goetz | ..................... | G06F 9/542 |
| 2021/0304891 A1* | 9/2021 | Kozloski | ............... | G16H 50/20 |
| 2021/0358579 A1* | 11/2021 | Chen | ...................... | G16H 10/60 |
| 2021/0383921 A1* | 12/2021 | Isobe | ..................... | G16H 20/00 |
| 2022/0198304 A1* | 6/2022 | Szczepanik | ............ | H04L 63/12 |
| 2022/0254513 A1* | 8/2022 | Chen | ..................... | G06N 20/20 |

FOREIGN PATENT DOCUMENTS

| | | |
|---|---|---|
| JP | 2019-193788 A | 11/2019 |
| WO | WO 2018/017467 A1 | 1/2018 |
| WO | WO 2019/211131 A1 | 11/2019 |

\* cited by examiner

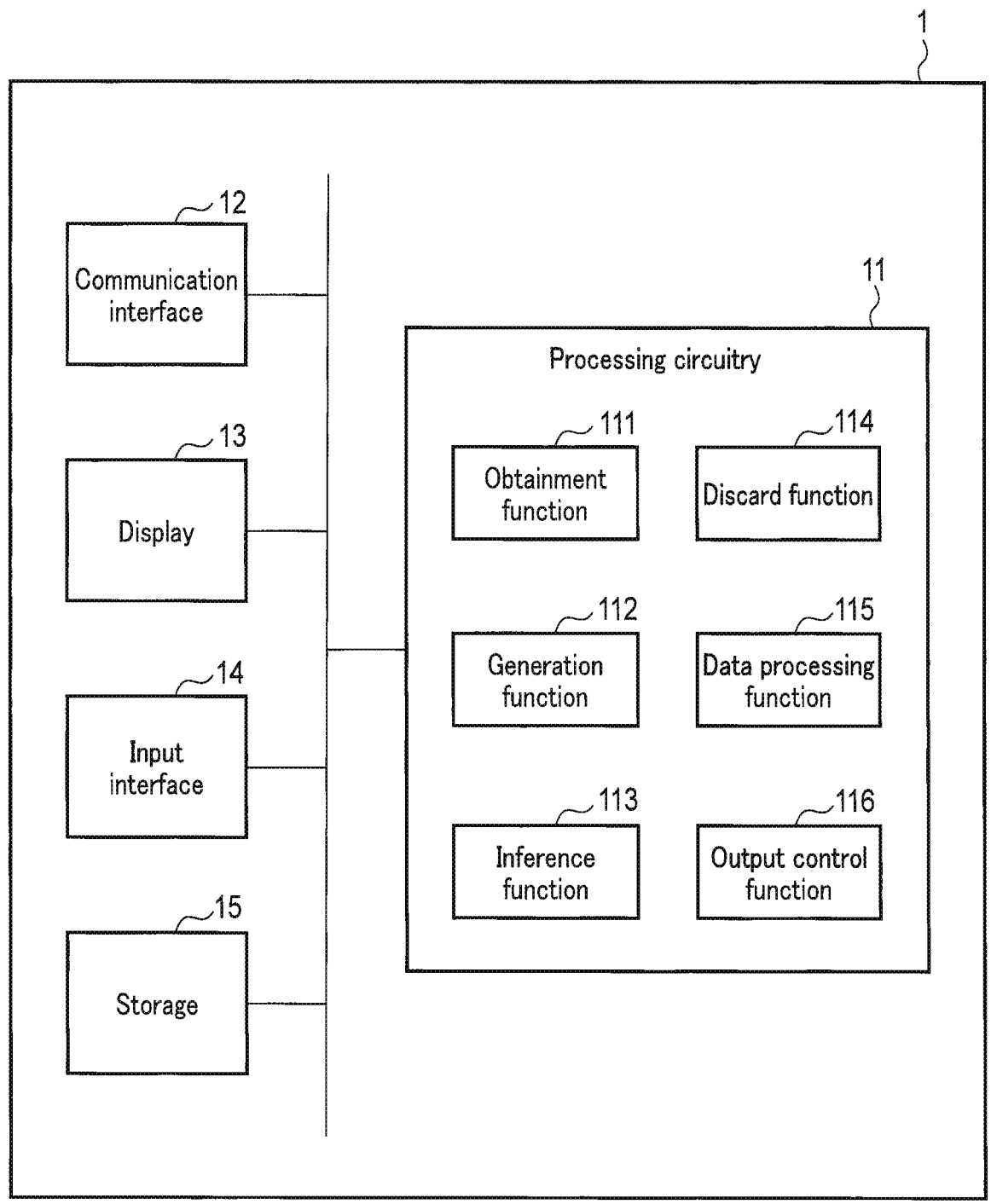
F I G. 1

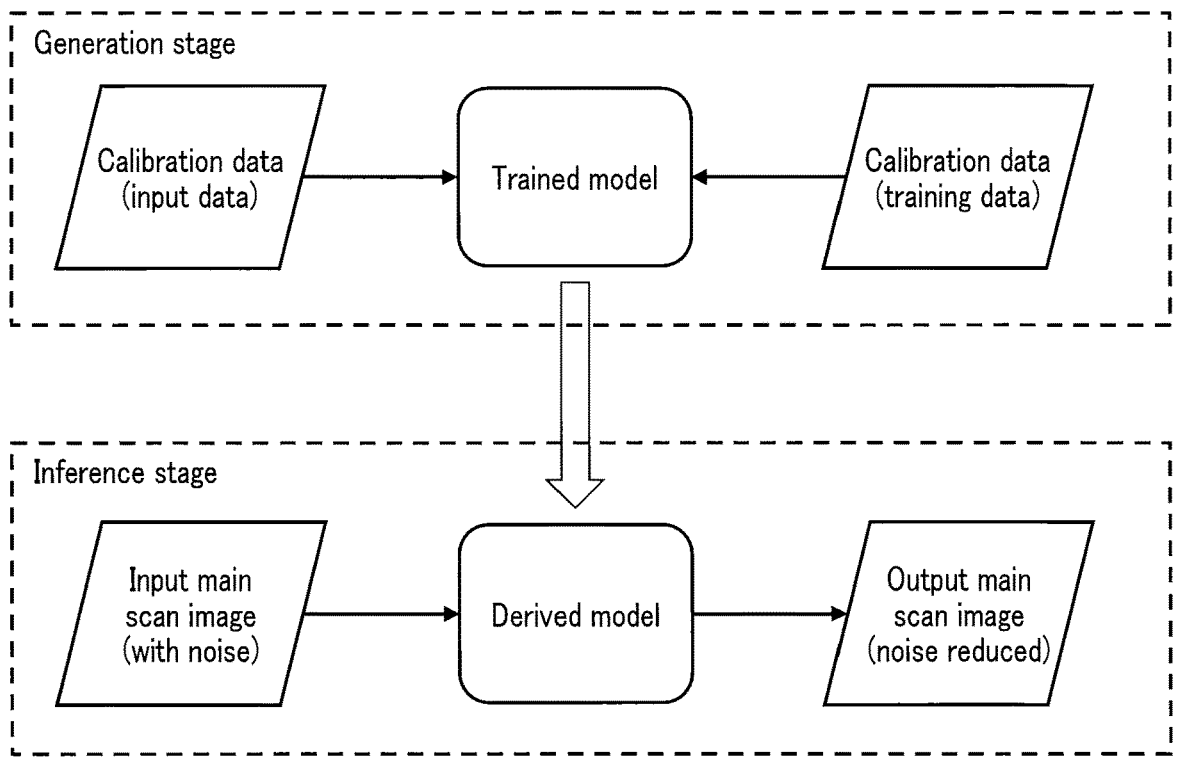
F I G. 4
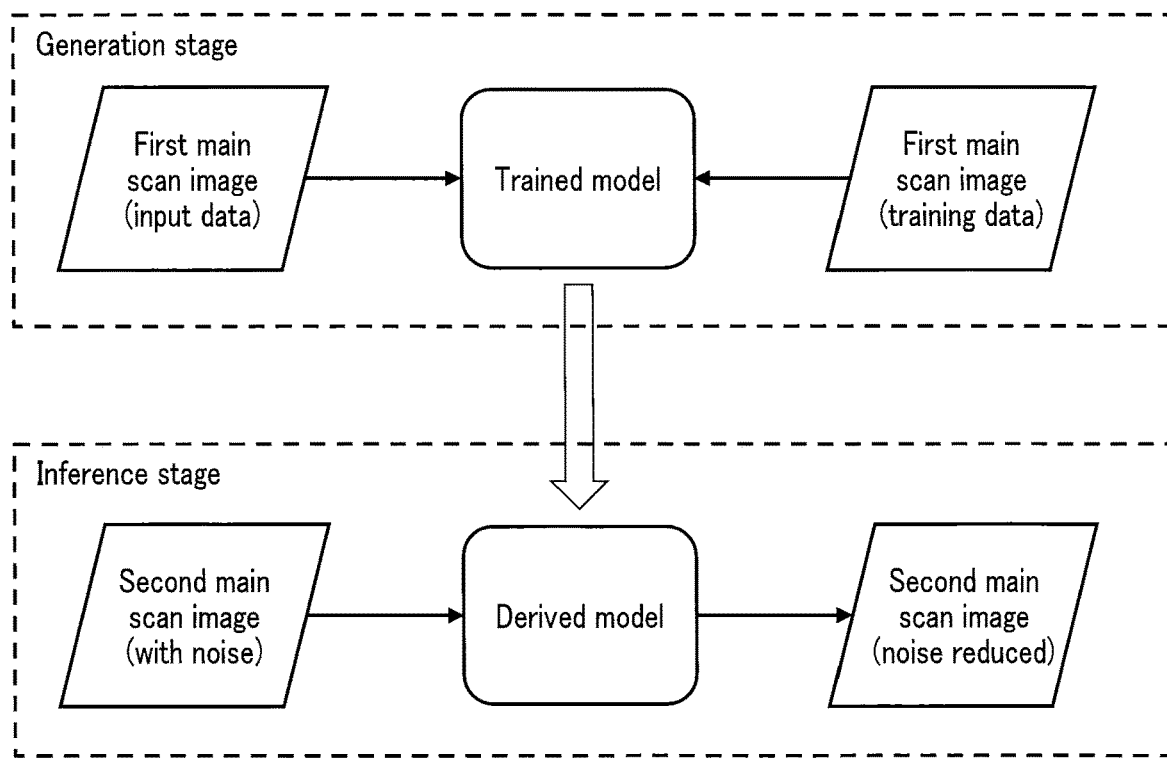
F I G. 5

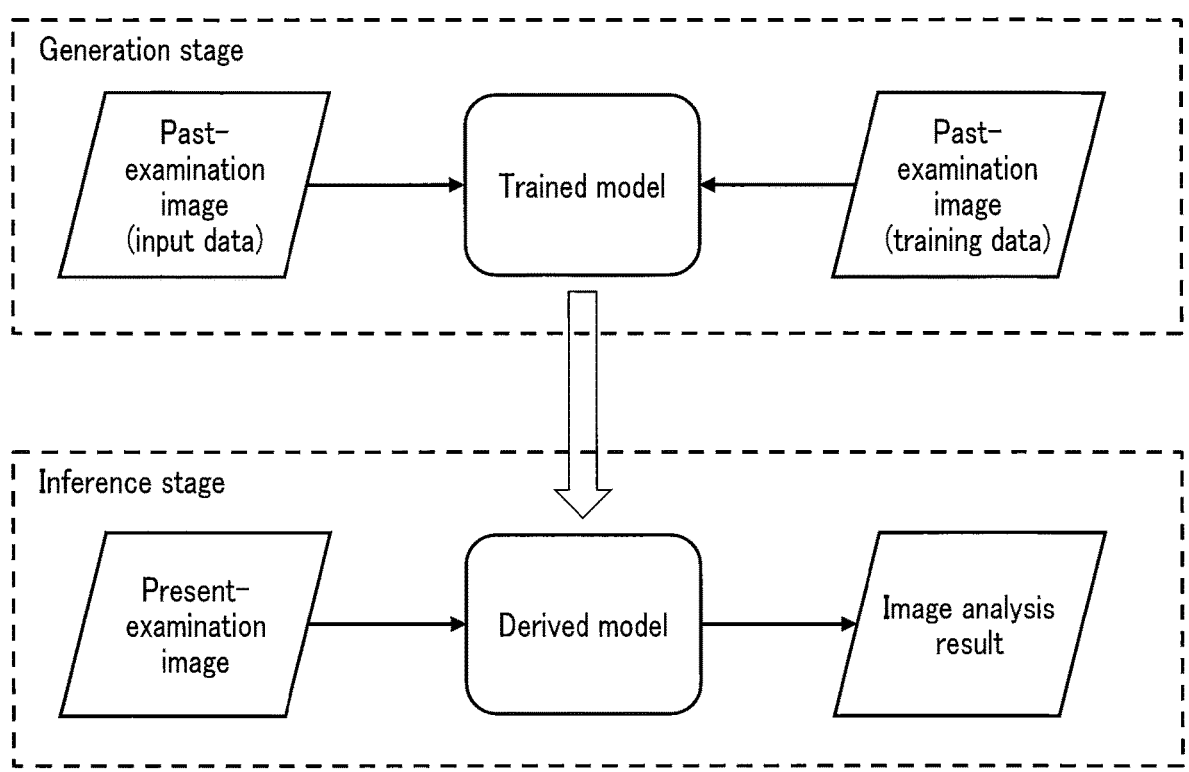
F I G. 9

MEDICAL DATA PROCESSING APPARATUS AND METHOD

CROSS-REFERENCE TO RELATED APPLICATION(S)

This application is based upon and claims the benefit of priority from prior Japanese Patent Application No. 2020-121510, filed Jul. 15, 2020, the entire contents of which are incorporated herein by reference.

FIELD

Embodiments described herein relate generally to a medical data processing apparatus and a medical data processing method.

BACKGROUND

Machine learning models are employed in various medical examinations for various subjects. Known machine learning types include an offline learning type and an online learning type. The offline learning type leaves parameters totally unupdated once the training process is complete, and as such, it cannot make the most of the capability of a machine learning inference model in individual examinations. The online learning type keeps updating parameters every time an examination is performed, and as such, it cannot guarantee that its performance is free from an incident where a preceding examination undesirably affects the inference result in a subsequent examination.

BRIEF DESCRIPTION OF THE DRAWINGS

FIG. 1 is a diagram showing a configuration of a medical data processing apparatus according to an embodiment.

FIG. 4 is a diagram schematically showing an exemplary process performed by the medical data processing apparatus according to Example 1.

FIG. 5 is a diagram schematically showing an overview of an exemplary process performed by a medical data processing apparatus according to Modification 1-1.

FIG. 9 is a diagram schematically showing an exemplary process performed by the medical data processing apparatus according to Example 2.

DETAILED DESCRIPTION

Figure 2:
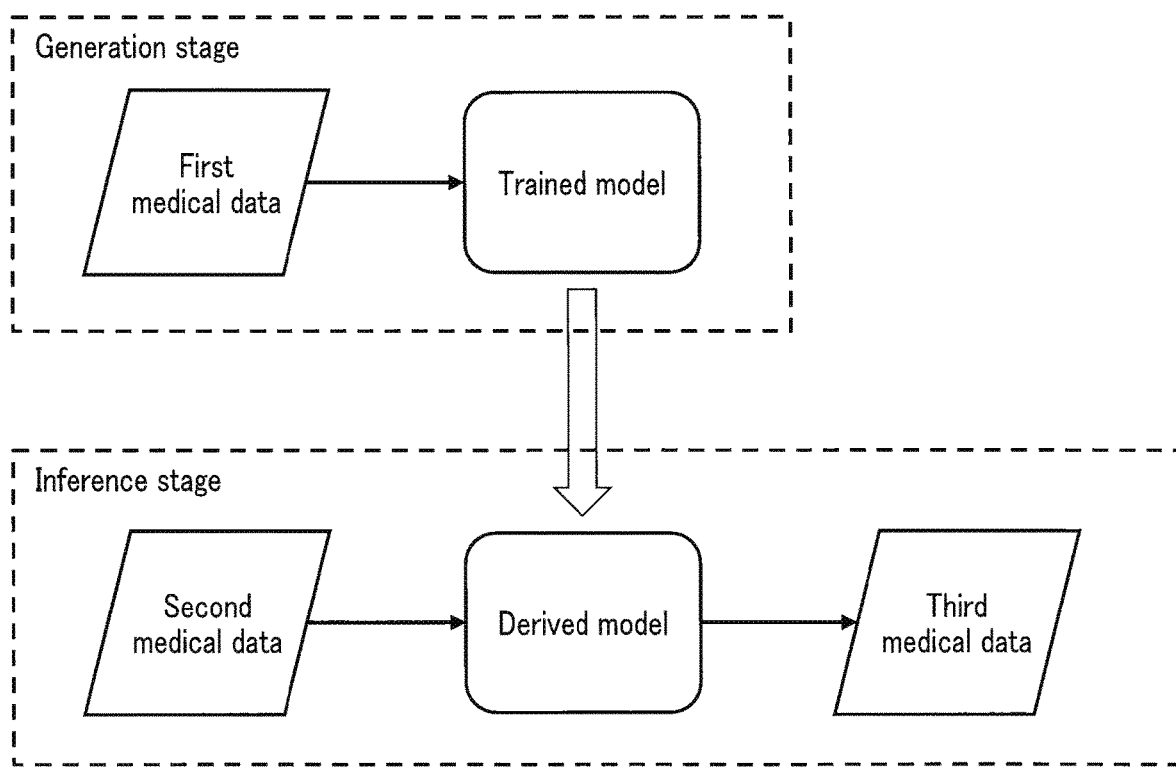
FIG. 2 is a diagram schematically showing an overview of an exemplary process performed by a medical data processing apparatus according to an embodiment.

According to an embodiment, a medical data processing apparatus includes a processing circuitry. The processing circuitry is configured to: obtain first medical data; generate, based on the first medical data, a derived model from a trained model; obtain second medical data for a same subject as a subject of the first medical data and with an acquisition parameter different from an acquisition parameter of the first medical data; and apply the second medical data to the derived model to generate third medical data.

Embodiments of the medical data processing apparatus and the medical data processing method will be described in detail with reference to the drawings.

The medical data processing apparatus according to an embodiment is, for example, a computer adapted to process medical data. The medical data is, for example, raw data or medical image data acquired by a medical apparatus. The medical apparatus is, for example, a medical image diagnostic apparatus. The medical image diagnostic apparatus may be a single-modality apparatus or a composite-modality apparatus. Examples of the single-modality apparatus include an X-ray computed tomography apparatus (X-ray CT apparatus), a magnetic resonance imaging apparatus (MRI apparatus), an X-ray diagnostic apparatus, a positron emission tomography (PET) apparatus, a single photon emission CT (SPECT) apparatus, an ultrasound diagnostic apparatus, an optical interference tomography apparatus (a fundus camera), and an optical ultrasound diagnostic apparatus. Examples of the composite-modality apparatus include a PET/CT apparatus, a SPECT/CT apparatus, a PET/MRI apparatus, and a SPECT/MRI apparatus. The medical apparatus may instead be an optical camera apparatus used as an accessory together with such a medical image diagnostic apparatus, or an optical camera apparatus attached to a catheter or the like.

Assuming that the medical image diagnostic apparatus is an X-ray CT apparatus, the X-ray CT apparatus at its gantry unit causes an X-ray tube to radiate X-rays toward a subject while rotating the X-ray tube and an X-ray detector around the subject. The X-rays that have transmitted through the subject are detected by the X-ray detector. The X-ray detector produces electric signals having wave-height values corresponding to doses of the detected X-rays. The electric signals are subjected to signal processing such as A/D conversion by data acquisition circuitry. The electric signals after the A/D conversion, etc. are called projection data or sinogram data. The X-ray CT apparatus at its console unit generates CT image data based on the projection data or the sinogram data. Such projection data, sinogram data, and CT image data are types of the medical data.

Assuming that the medical image diagnostic apparatus is an MRI apparatus, the MRI apparatus at its gantry unit repeats application of a gradient magnetic field via a gradient magnetic field coil and application of an RF pulse via a transmission coil, under the application of a static magnetic field via a static magnetic field magnet. In response to the RF pulse application, the subject releases MR signals. The released MR signals are received via a reception coil. The received MR signals are subjected to signal processing such as A/D conversion by reception circuitry. The MR signals after the A/D conversion, etc. are called k-space data. The MRI apparatus at its console unit generates MR image data based on the k-space data. Such k-space data and MR image data are types of the medical data.

Assuming that the medical image diagnostic apparatus is an ultrasound diagnostic apparatus, the ultrasound diagnostic apparatus causes an ultrasound probe to send ultrasound beams using multiple ultrasound vibrators toward the inside of a subject body, and to receive ultrasound waves reflected from the inside of the subject body using the ultrasound vibrators. The ultrasound vibrators produce electric signals having wave-height values corresponding to sound pressures of the received ultrasound waves. The electric signals are subjected to signal processing such as A/D conversion by an A/D converter arranged at the ultrasound probe or other location. The electric signals after the A/D conversion, etc. are called echo data. The ultrasound diagnostic apparatus at its main unit generates ultrasound image data based on the echo data. Such echo data and ultrasound image data are types of the medical data.

Assuming that the medical image diagnostic apparatus is a PET apparatus, the PET apparatus at its gantry unit simultaneously measures, using coincidence circuitry, a pair of 511-keV gamma rays generated due to an annihilation event between positrons generated from radionuclides accumulated in a subject and electrons present around the radionuclide, so that it generates digital data including digital values indicative of the energy value and the detection position for the pair of gamma rays. This digital data is called coincidence data or sinogram data. The PET apparatus at its console unit generates PET image data based on the coincidence data or the sinogram data. Such coincidence data, sinogram data, and PET image data are types of the medical data.

Assuming that the medical image diagnostic apparatus is an X-ray diagnostic apparatus, the X-ray diagnostic apparatus causes an X-ray tube arranged at its C-arm to generate X-rays. The X-rays generated by the X-ray tube and having transmitted through the subject are received by an X-ray detector such as a flat panel display (FPD) arranged at the C-arm or separately from the C-arm. The X-ray detector produces electric signals having wave-height values corresponding to doses of the detected X-rays, and subjects the electric signals to signal processing such as A/D conversion. The electric signals after the A/D conversion, etc. are called projection data or X-ray image data. In the course of cone-beam CT, etc., such projection data or X-ray image data is used as raw data. The projection data and the X-ray image data are types of the medical data.

The embodiments do not limit the raw data to original raw data acquired by each medical image diagnostic apparatus. For example, the raw data may be computational raw data that can be obtained through a process of applying the reverse transformation technique to medical images. Supposing that original raw data has been acquired by an X-ray CT apparatus, the reverse transforming process may be, for example, the Radon transform. Supposing that original raw data has been acquired by an MRI apparatus, the reverse transforming process may be, for example, Fourier transformation. The raw data in each embodiment may also be raw data that has undergone one or more data processing operations from the original. Such one or more data processing operations may be any of the various operations including noise reduction, data compression, resolution decomposition, data interpolation, resolution synthesis, super-resolution processing, and so on.

FIG. 1 is a diagram showing an exemplary configuration of a medical data processing apparatus 1 according to an embodiment. The medical data processing apparatus 1 may be an internal computer of a medical apparatus or a computer separate from the medical apparatus.

As shown in FIG. 1, the medical data processing apparatus 1 includes processing circuitry 11, a communication interface 12, a display 13, an input interface 14, and a storage 15.

The processing circuitry 11 includes a processor such as a central processing unit (CPU). The processor runs various programs installed in the storage 15 or other locations to implement various functions including an obtainment function 111, a generation function 112, an inference function 113, a discard function 114, a data processing function 115, an output control function 116, etc. The functions 111 to 116 are not limited to implementation through a single processing circuitry component. Multiple independent processors may be employed together to form the processing circuitry so that the processors run the programs to realize the respective functions 111 to 116.

By implementing the obtainment function 111, the processing circuitry 11 obtains medical data for a subject. More specifically, the processing circuitry 11 obtains raw data, medical image data, etc., from the medical apparatus. The processing circuitry 11 may obtain medical data that has been collected via the communication interface 12 or a portable storage medium, etc. and stored in the storage 15. The processing circuitry 11 obtains first medical data. Also, the processing circuitry 11 obtains second medical data for a same subject as the subject of the first medical data and with an acquisition parameter different from the acquisition parameter of the first medical data. The obtainment function 111 is one example of a first obtaining unit and a second obtaining unit.

By implementing the generation function 112, the processing circuitry 11 generates, based on the first medical data, a derived model from a trained model. The trained model is, for example, a learning model which has been generated in advance by the medical data processing apparatus 1 or other computers and stored in the storage 15. Such a trained model may be a machine learning model that has been trained based on multiple training samples for multiple subjects. A machine learning model refers to a multi-layered neural network, in other words, a parameterized composite function. The composite function here includes parameters as coefficients. The description will call a parameter included in a machine learning model an "adjustment parameter". In the disclosure herein, the trained models are not limited to particular processing contents. For example, each trained model may be intended to reduce noise in medical data, to output a result of various image analyses based on medical data, or to perform image recognition processes with medical data. The machine learning model may be furnished as a program, or may be physically incorporated as an integrated circuit to realize the intended functions thereof. The generation function 112 is one example of a generator.

By implementing the inference function 113, the processing circuitry 11 applies medical data to the derived model to generate output medical data. In an exemplary configuration, the processing circuitry 11 applies the second medical data to the derived model to generate third medical data. The third medical data depends on the processing performed with the derived model and the trained model. The inference function 113 is one example of an applicator.

By implementing the discard function 114, the processing circuitry 11 disposes of the derived model. More specifically, the processing circuitry 11, after using the derived model by the inference function 113, saves a dump of the derived model in the storage 15 and discards (erases) the derived model. The discard function 114 is one example of a discard unit.

By implementing the data processing function 115, the processing circuitry 11 subjects medical data to various types of data processing. Such data processing may include, when the medical data is raw data, various types of preprocessing for the raw data and conversion of the raw data into image data. When the medical data is image data, the data processing may include various types of image processing for the image data. Examples of the image processing include volume rendering, surface volume rendering, pixel value projection, multi-planer reconstruction (MPR), curved MPR (CPR), and so on. The image processing may also include processing for display, such as gradation processing, zooming in and out, and so on. The data processing function 115 is one example of a data processor.

By implementing the output control function 116, the processing circuitry 11 presents medical data through the display 13. In an exemplary configuration, the processing circuitry 11 causes the third medical data from the derived model to be displayed. The output control function 116 is one example of an outputter.

The communication interface 12 is an interface adapted to connect the medical apparatus with a workstation, a picture archiving and communication system (PACS), a hospital information system (HIS), a radiology information system (RIS), etc., via a local area network (LAN) or the like. Such a network enables communicating various sets of information among the connected workstation, PACS, HIS, RIS, etc. The communication interface 12 is one example of a communicator.

The display 13 displays various data sets according to the output control function 116 of the processing circuitry 11. The display 13 may discretionarily be a liquid crystal display (LCD), a cathode-ray tube (CRT) display, an organic electroluminescence display (OELD), a plasma display, or any other display available. The display 13 may instead be a projector. The display 13 may constitute one example of the outputter.

The input interface 14 receives various input operations from a user and converts the received input operations into electric signals for output to the processing circuitry 11. More specifically, the input interface 14 is coupled to one or more input devices such as a mouse, a keyboard, a track ball, a switch, buttons, a joystick, a touch pad, and a touch panel display. The input interface 14 outputs the electric signals corresponding to the input operations received by such input devices to the processing circuitry 11. Note that the input devices coupled to the input interface 14 may each be an input device furnished at an external computer connected via a network, etc. The input interface 14 may also be a voice recognition device adapted to receive voice signals via a microphone and convert the voice signals into command signals. The input interface 14 is one example of an inputter.

The storage 15 is a memory device adapted to store various types of data sets, such as a read-only memory (ROM), a random-access memory (RAM), a hard disk drive (HDD), a solid state drive (SSD), and an integrated circuit memory device. The storage 15 stores, for example, raw data and various medical images, as well as various machine learning models. Other than such memory devices, the memory 15 may be any one or combination of portable memory devices such as a compact disc (CD), a digital versatile disc (DVD), and a flash memory, or a driver that reads and writes various types of information in cooperation with semiconductor memory devices. The storage 15 may be located within an external computer connected to the medical data processing apparatus 1 via a network. The storage 15 is one example of a storage.

The medical data processing apparatus 1 according to the embodiment will be described in further detail.

FIG. 2 is a diagram schematically showing an overview of an exemplary process performed by the medical data processing apparatus 1 according to the embodiment. As shown in FIG. 2, the process in the embodiment may be divided into a generation stage and an inference stage. In the generation stage, a derived model is generated from a trained model based on first medical data. This derived model generation is conducted through training of one or more adjustment parameters of the trained model based on the first medical data. In the inference stage, second medical data is applied to the derived model so that third medical data is generated. The second medical data is related to the same subject as that of the first medical data, but at least one acquisition parameter is different between the first medical data and the second medical data. The first medical data and the second medical data are items of medical data which are acquired in the same examination, or in separate, respective examinations which can be deemed comparable in respect of morphology of the associated anatomical structure. For example, when the first medical data and the second medical data have been acquired in the same examination, the medical data acquired by a scanning action (imaging operation) performed after the scanning action for the first medical data serves as the second medical data. Also for example, when the first medical data and the second medical data have been acquired in separate examinations, the medical data acquired in the examination performed after the examination for the first medical data serves as the second medical data. Note that, in the context of the embodiment, the term "first medical data" represents medical data for use in generation of a derived model, the term "second medical data" represents medical data for input to a derived model, and the term "third medical data" represents medical data output from a derived model.

Acquisition parameters of medical data may include any one of a corresponding examination date and time, scan date and time, slice position, image reconstructing technique, field of view (FOV), scan site, temporal resolution, matrix size, level (presence/absence) of a contrast medium, and scan conditions. The scan conditions include various parameters according to the type of the medical image diagnostic apparatus. When an MRI apparatus is adopted, the scan conditions may further include, for example, particulars of a scan sequence and scan contrasts, parameters such as time to repeat (TR), echo time (TE), and flip angle (FA), and particulars of a k-space filling trajectory. In the instances of X-ray CT, the scan conditions may further include X-ray conditions (values of tube current and tube voltage, and duration of X-ray radiation, etc.), a scan type (non-helical scan, helical scan, gated scan, etc.), a tilt angle, reconstruction functions, a view number per one rotation of the rotary frame, a rotational speed of the rotary frame, and spatial resolution of the detector. In the instances of ultrasound diagnoses, the scan conditions may include a focal position, a gain, transmission intensity, reception intensity, PRF, and types of beam-scanning technique (sector scan, convex scan, linear scan, etc.) and scan mode (B-mode scan, Doppler scan, color Doppler scan, M-mode scan, A-mode scan, etc.).

As will be described, in typical implementation, the first medical data and the second medical data are medical data generated by one or more medical image diagnostic apparatuses according to the same imaging principle or modality.

As one example, when an X-ray CT apparatus performs a scanning action for positioning and then a main scanning operation in the context of a single examination for a single subject, the positioning image may be used as the first medical data and the X-ray CT image may be used as the second medical data. As another example, when an X-ray CT apparatus acquires X-ray CT images of multiple time-series frames while rotating its gantry unit multiple times, an X-ray CT image of the N-th frame (N being an index indicating a frame number) may be used as the first medical data and an X-ray CT image of the (N+n)-th frame (n being any integer equal to or greater than 1) as the second medical data. As yet another example, when an X-ray CT apparatus performs a volume scan and acquires three-dimensional X-ray CT image data, a two-dimensional X-ray CT image at the M-th slice (M being an index indicating a slice number) may be used as the first medical data and a two-dimensional X-ray CT image at the (M+m)-th slice (m being any integer equal to or greater than 1) as the second medical data. As a further example, when an X-ray CT apparatus performs a dual-energy scan, an X-ray CT image of a low tube voltage may be used as the first medical data and an X-ray CT image of a high tube voltage may be used as the second medical data, or vice versa (using an X-ray CT image of a high tube voltage as the first medical data and using an X-ray CT image of a low tube voltage as the second medical data).

The embodiments are not limited to X-ray CT apparatuses, but may likewise be applicable to implementation with any other medical image diagnostic apparatuses such as an MRI apparatus and an ultrasound diagnostic apparatus. As one example of such other instances, when an ultrasound diagnostic apparatus performs a B-mode volume scan and then a B-mode two-dimensional scan in the context of a single examination for a single subject, the three-dimensional B-mode image may be used as the first medical data and the two-dimensional B-mode image may be used as the second medical data. As another example, when an ultrasound diagnostic apparatus performs a color Doppler scan for a blood flow and then a color Doppler scan for a low-speed blood flow, the normal-speed blood flow image may be used as the first medical data and the low-speed blood flow image may be used as the second medical data.

The first medical data and the second medical data are not required to be medical data generated by one or more medical image diagnostic apparatuses according to the same imaging principle or modality. The first medical data and the second medical data may be any medical data as long as they are acquired in the same examination or in separate examinations which can be deemed comparable in respect of morphology of the associated anatomical structure. As one example, when an X-ray CT apparatus performs an X-ray CT scan and then an MRI apparatus performs an MR scan in the context of a single examination for a single subject, the X-ray CT image may be used as the first medical data and the MR image may be used as the second medical data. As another example, when an X-ray CT apparatus performs an X-ray CT scan and then an X-ray diagnostic apparatus performs an X-ray fluoroscopy in the context of an operation for a single subject, the X-ray CT image may be used as the first medical data and the X-ray fluoroscopic image may be used as the second medical data. As yet another example, when an X-ray CT apparatus performs an X-ray CT scan and then an ultrasound diagnostic apparatus performs an ultrasound scan in the context of an operation for a single subject, the X-ray CT image may be used as the first medical data and the ultrasound image may be used as the second medical data. Only non-limiting examples have been described, and the medical image diagnostic apparatuses mentioned above may be discretionarily replaced with any desired medical image diagnostic apparatuses.

The embodiment assumes trained models to be machine learning models generated through offline training processes. The trained models according to the embodiment, are neither untrained models nor models in the ongoing training for the purpose of online training, but are machine learning models which have been generated through offline training processes. Each trained model is set with one or more trained parameters. In an exemplary implementation, the trained model may be assigned a flag indicative of completion of its training process. Also, the trained model may be assigned any identification information, etc., such as a unique identifier, version information, date and time it was trained, and date and time it was installed. The trained models are stored in the storage 15 at the delivery or maintenance of the product. Also, the trained models may instead or additionally be obtained by later purchase, etc., and stored in the storage 15 as a downloaded object from a desired computer or the like via the communication interface 12, or from a portable recording medium or other computer devices.

The trained models may each be a machine learning model with one or more adjustment parameters that have been trained based on multiple training samples for multiple subjects, so that the trained models are generalized to many subjects. The trained models are stored in the storage 15 for regular use in the medical data processing apparatus 1. A derived model is generated from the applicable trained model. To generate the derived model, one or more adjustment parameters of the trained model are changed based on the first medical data for the subject that is a target of inference. More specifically, the derived model is generated through the process of altering a default adjustment parameter of the trained model by training it based on the first medical data, and applying the altered adjustment parameter to the machine learning model. The derived model may be understood as a machine learning model that is adaptably fit and tailored to the inference target subject. Such a derived model is a temporary-use machine learning model used only in a single examination for the inference target subject. Generation of each derived model requires a significantly reduced amount of medical data as compared to generation of the corresponding trained model, and as such, the derived model is a suitable adaptation for the inference target subject. The second medical data is therefore not applied to the trained model but applied to the derived model, so that better inference results can be obtained.

In typical implementations, the medical data processing apparatus 1 according to the embodiment is either mounted on a medical image diagnostic apparatus or set at a work station. Below, Example 1 and Example 2 will be described, assuming that the former is a form in which the medical data processing apparatus 1 is mounted on a medical image diagnostic apparatus and the latter is a form in which it is set at a work station. Unless otherwise mentioned, the medical image diagnostic apparatus in the examples will be assumed to be an MRI apparatus. However, each example is not limited to the implementation with an MRI apparatus, but may be discretionarily applied to the implementation with any medical apparatuses.

Example 1

Example 1 assumes that the medical data processing apparatus 1 is mounted on an MRI apparatus. Also, while processing contents of the machine learning models are not limited, this example assumes that the employed machine learning model is for reducing noise in medical images. Exemplary processing other than noise reduction processing will be described as modifications, as appropriate and without intention to limit.

Figure 3:
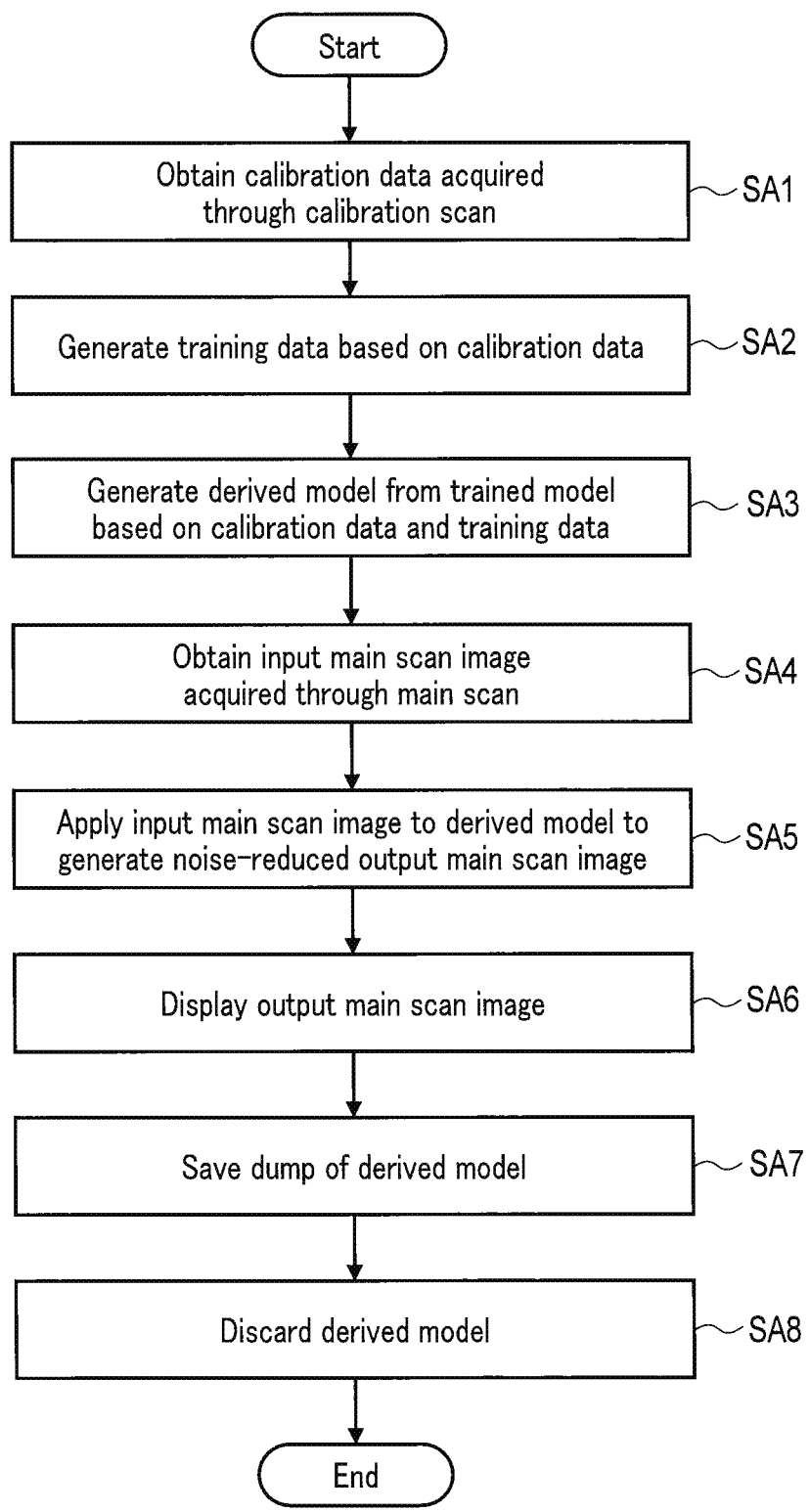
FIG. 3 is a diagram showing a typical flow of an exemplary process performed by a medical data processing apparatus according to Example 1.

FIG. 3 is a diagram showing a typical flow of an exemplary process performed by the medical data processing apparatus 1 according to Example 1. FIG. 4 is a diagram schematically showing an exemplary process performed by the medical data processing apparatus 1 according to Example 1.

As shown in FIGS. 3 and 4, the processing circuitry 11 in the generation stage implements the obtainment function 111 to obtain calibration data acquired through a calibration scan (step SA1). The calibration data is medical data acquired by the MRI apparatus performing, before a main scanning operation, a calibration scan for the inference target subject. The calibration data is used as input data for generating the derived model. The calibration data is one example of the first medical data. The calibration scan may be performed for any purposes including obtaining a B0 map and a B1 map, obtaining a sensitivity distribution map, obtaining a noise level, and so on. Here, the B0 map shows a spatial distribution of phase values of the static magnetic field. The B1 map shows a spatial distribution of phase values of the transmission magnetic field. The sensitivity distribution map shows a spatial distribution of sensitivity values of the reception coil.

After step SA1, the processing circuitry 11 implements the generation function 112 to generate, based on the calibration data obtained in step SA1, training data (step SA2). The processing circuitry 11 in this step SA2, for example, subjects the B0 or B1 map to a noise reduction process with an image filter, etc. to generate a noise-reduced B0 or B1 map. The noise-reduced B0 or B1 map is used as training data to the B0 or B1 map obtained in step SA2.

After step SA2, the processing circuitry 11 implements the generation function 112 to generate, based on the calibration data obtained in step SA1 and the training data generated in step SA2, a derived model from the trained model (step SA3). More specifically, the processing circuitry 11 generates the derived model by changing an adjustment parameter of the trained model based on the calibration data and the training data. This generation process may employ error propagation techniques, etc. The processing circuitry 11 here performs forward propagation using the trained model for the input data, i.e., the calibration data obtained in step SA1, to output estimated data. The processing circuitry 11 then performs back-propagation using the trained model for an error between the output estimated data and the training data, to calculate a gradient to a loss function for the adjustment parameter. The processing circuitry 11 changes the adjustment parameter of the trained model based on the gradient. By changing the adjustment parameter of the trained model, a derived model different from the trained model is generated.

Datasets for the training process to generate derived models may be, for example, a pair of training samples constituted by calibration data (input data) as obtained in step SA1 and training data as generated in step SA2, or multiple training samples constituted by such a training sample pair and additional training samples obtained by duplicating training data prepared beforehand.

Training conditions in the generation stage may be the same as those adopted in the training process for the trained model. The training conditions include, for example, training coefficients, error functions, optimization algorithms, etc. The training conditions that have been used in training processes are, for example, stored in the storage 15 in association with the corresponding trained models. Note that the training conditions in the generation stage and the training conditions adopted in the training process are not required to be completely the same, and a change may be introduced as desired.

For the process to generate derived models, it is not required to change all the adjustment parameters of one trained model, but only a specific adjustment parameter or parameters may be changed as a change target. In one example, the processing circuitry 11 sets some of the adjustment parameters of a trained model as fixed parameters and the remaining adjustment parameters as change target parameters. The number of the change target parameters is not particularly limited, but supposing an exemplary configuration where a trained model involves 20 layers, it is preferable that adjustment parameters for as many as one or two layers be set as change target parameters. The change target parameters are not required to correspond to particular positions or portions in the trained model, either. The change target parameters may correspond to one or two layers on the input side, one or two layers on the output side, or one or two intermediate layers. The change target parameters may also be dispersively set.

Upon step SA3, the processing circuitry 11 enters the inference stage and implements the obtainment function ill to obtain an MR image acquired through a scanning operation (main scan) (step SA4). The MR image obtained in step SA4 will be called an "input scan image", as it is used as input data to the derived model. The input scan image is medical data acquired by the MRI apparatus performing a scanning operation after the calibration scan. This scanning operation is a main scan for acquiring contrast-enhanced images such as T1-weighted images, T2-weighted images, and proton density-weighted images. The scan subject here is the same as the subject of the calibration scan. The scan site of the main scan is included in the range of the calibration scan. As such, the morphology of the anatomical structure showed on the input scan image can be deemed substantially the same as the morphology of the anatomical structure showed on the calibration data. The input scan image and the calibration data differ from each other in acquisition parameters such as a scan date and time, particulars of scan sequences and scan contrasts, etc. The input scan image is one example of the second medical data.

The MR image from the main scan may be generated by either the MRI apparatus or the medical data processing apparatus 1. In the instance of the former, the MRI apparatus acquires k-space data by a main scan, subjects the k-space data to reconstruction processing to generate an MR image, and sends the MR image to the medical data processing apparatus 1. In the instance of the latter, the MRI apparatus acquires k-space data by a main scan and sends the k-space data to the medical data processing apparatus 1, so that the processing circuitry 11 of the medical data processing apparatus 1 implements the data processing function 115 to subject the k-space data to reconstruction processing to generate an MR image.

After step SA4, the processing circuitry 11 implements the inference function 113 to apply the input scan image obtained in step SA4 to the derived model generated in step SA3, so as to generate a noise-reduced MR image (hereinafter, an "output scan image") (step SA5). The output scan image is one example of the third medical data.

After step SA5, the processing circuitry 11 implements the output control function 116 so that the output scan image generated in step SA5 is presented (step SA6). In an exemplary implementation, the display 13 is caused to display the output scan image. The processing circuitry 11 here may perform a control to display the output scan image together with a message indicating the use of the derived model.

After step SA6, the processing circuitry 11 implements the discard function 114 so that a dump of the derived model is saved (step SA7). Such a dump retains all the information related to the derived model. For example, a dump may contain various data sets including adjustment parameters for the corresponding derived model, data that occurred when the output scan image was generated using the derived model in step SA5, and so on. Dumps are stored in the storage 15 in association with respective identifiers of the derived models. Saving a dump before discarding the corresponding derived model enables later verification based on the analysis of the dump, in the event that the medical data processing apparatus 1 experiences a failure and the verification of the processing that has used the derived model is necessary.

After step SA7, the processing circuitry 11 implements the discard function 114 to discard the derived model (step SA8). The processing circuitry 11 in this step SA8 makes the derived model unusable by, for example, erasing the data of the derived model from the storage 15 or other memories. The processing circuitry 11 may set an expiration time stamp for the derived model so that the derived model is automatically erased upon elapse of a predetermined time from its generation. The predetermined time may be a sum of a time period which is normally required for an operational flow to proceed from completion of the generation of a derived model in step SA3 up to completion of the inference in step SA5, and a margin time. The processing circuitry 11, upon detecting the elapse of the predetermined time, erases the derived model.

The process performed by the medical data processing apparatus 1 according to Example 1 therefore comes to the end.

As described above, according to Example 1, the processing circuitry 11 generates a derived model from a trained model using first medical data acquired in an examination, and applies second medical data acquired in the same examination with a different parameter to the derived model. Here, the trained model has been generated through an offline training process, and the derived model, to which the second medical data is applied, is generated by the processing circuitry 11 from the trained model based on the first medical data acquired in the same examination for the same subject as those of the second medical data. The derived model as such is suitably tailored to the subject. Accordingly, it is possible to make the most of the capability of the machine learning inference model in individual examinations. Also, since the derived model is generated using only the first medical data acquired in a specific examination for a specific subject, and the trained model itself is not updated, the changes in one or more adjustment parameters of the trained model will not be handed down to other examinations. Accordingly, it is possible to guarantee that the performance of the machine learning model is free from an incident where a preceding examination undesirably affects the inference result in a subsequent examination. That is, the inference capability can be improved while steady performance is guaranteed. Note that, also for the sake of this performance guarantee, the processing circuitry 11 discards each derived model after the use thereof.

The foregoing example does not intend any limitation. Various modifications are possible.

Modification 1-1

FIG. 5 is a diagram schematically showing an overview of an exemplary process performed by the medical data processing apparatus 1 according to Modification 1-1. As shown in FIG. 5, the processing circuitry 11 according to Modification 1-1 generates, in the generation stage, a derived model from the trained model based on an MR image acquired through a first scan (hereinafter, a "first scan image"). In an exemplary configuration, the first scan image that has not undergone a noise reduction process is set as input data, and the first scan image that has undergone a noise reduction process is set as training data, so that the derived model is generated from the trained model based on the input data and the training data. The first scan image is one example of the first medical data.

As shown in FIG. 5, the processing circuitry 11 in the inference stage applies an MR image acquired through a second scan (hereinafter, an "input second scan image") to the derived model, so as to generate a noise-reduced MR image (hereinafter, an "output second scan image"). The input second scan image is one example of the second medical data, and the output second scan image is one example of the third medical data. The first scan is a scanning operation performed by the MRI apparatus before the second scan. The first scan and the second scan are main scans conducted on the same subject as an imaging target. The first scan and the second scan differ from each other in acquisition parameters such as imaging contrasts, scan sequences, etc. Thus, the first scan image and the input second scan image are related to the same subject while differing in acquisition parameters.

According to Modification 1-1, a derived model is generated from a trained model based on a first scan image, and an input second scan image is applied to the derived model so as to generate a noise-reduced output second scan image. The first scan image has a signal-to-noise ratio (SNR) higher than that of calibration data. Thus, use of the first scan image for generating a derived model from the trained model would endow the derived model with enhanced processing accuracy. Types of the first scan image and the input second scan image are not particularly limited. For example, a preferable result can also be expected from the case where the first scan is a scanning operation for acquiring a proton density-weighted image and the second scan is a scanning operation for acquiring a T1-weighted image or a T2-weighted image. The proton density-weighted image has a relatively high SNR. Thus, use of the proton density-weighted image for generating a derived model from the trained model would also endow the derived model with enhanced processing accuracy.

Modification 1-2

The foregoing examples are applicable also to parallel imaging (PI) technique. Modification 1-2 will assume a scan sequence complying with parallel imaging according to an image-space method, such as sensitivity encoding (SENSE).

A brief description will be given of how the imaging is performed in the parallel imaging according to an image-space method. In the parallel imaging according to an image-space method, an MRI apparatus conducts a calibration scan on a subject to acquire k-space data for each of multiple coils for obtaining a sensitivity distribution map. The MRI apparatus generates multiple sensitivity distribution maps corresponding to the respective coils based on the acquired k-space data sets. The MRI apparatus then conducts, on the same subject, a sparse scan or an under-sampled scan that omits some of the k-space lines and generates multiple aliasing images corresponding to the respective coils. The k-space lines here indicate data acquisition trajectories in the k-space. The aliasing images here are MR images involving aliasing artifacts originating from the omission of k-space lines. The MRI apparatus performs application processing based on the multiple aliasing images and sensitivity distribution maps to generate a single MR image without aliasing (hereinafter, a "PI image"). Such a PI image is an MR image with reduced signal losses due to sensitivity unevenness among the coils, and also reduced aliasing artifacts.

Figure 6:
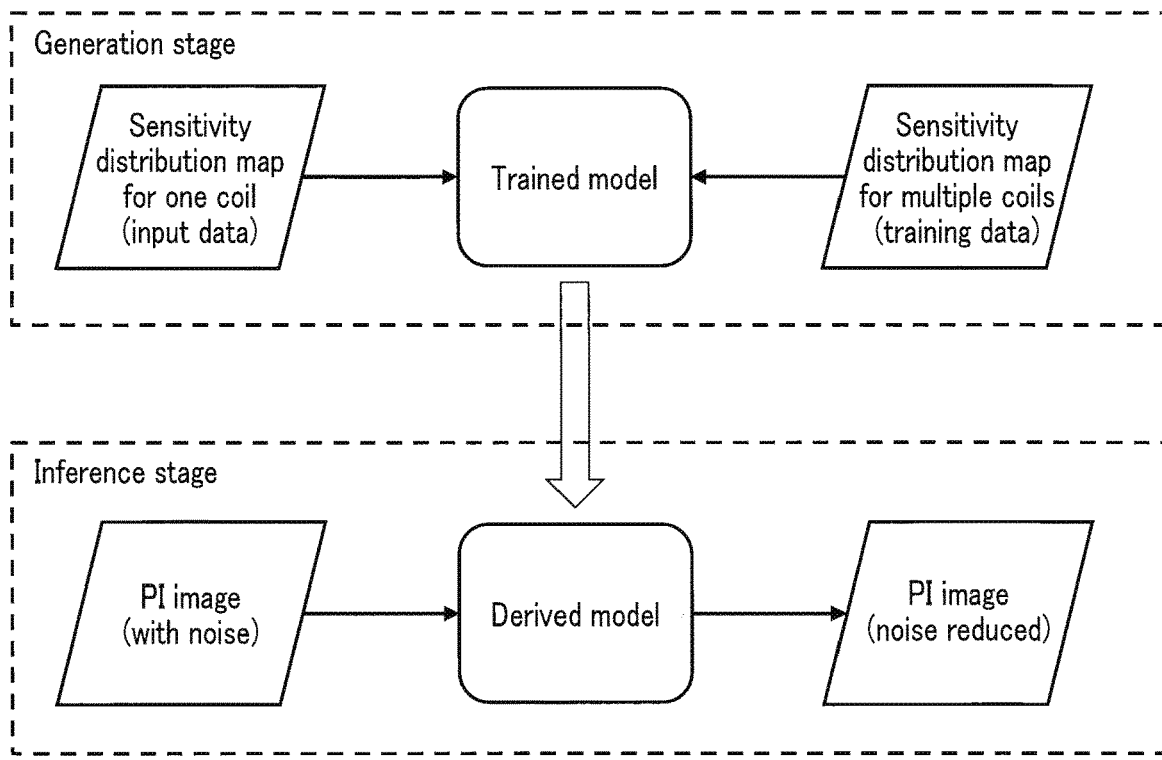
FIG. 6 is a diagram schematically showing an overview of an exemplary process performed by a medical data processing apparatus according to Modification 1-2.

FIG. 6 is a diagram schematically showing an overview of an exemplary process performed by the medical data processing apparatus 1 according to Modification 1-2. As shown in FIG. 6, the processing circuitry 11 according to Modification 1-2 obtains, in the generation stage, multiple sensitivity distribution maps corresponding to respective coils. The processing circuitry 11 selects a sensitivity distribution map for any one coil from these multiple sensitivity distribution maps, automatically or as manually directed via the input interface 14. Such a sensitivity distribution map for one coil is one example of the first medical data. The sensitivity distribution map for one coil is set as input data. Also, the processing circuitry 11 subjects the multiple sensitivity distribution maps corresponding to the respective coils to summation processing to generate a sensitivity distribution map for the multiple coils. This sensitivity distribution map for the multiple coils is set as training data. The processing circuitry 11 generates, based on the input data and the training data, a derived model from a trained model.

In the inference stage, as shown in FIG. 6, the processing circuitry 11 obtains a PI image acquired through an under-sampled scan in k-space. It will be assumed that this PI image has not undergone post-processing and includes noise. The processing circuitry 11 applies the PI image including noise to the derived model to generate a noise-reduced PI image. The PI image with noise is one example of the second medical data, and the noise-reduced PI image is one example of the third medical data. The sensitivity distribution map for one coil and the PI image differ from each other in acquisition parameters such as image reconstruction methods. Thus, the sensitivity distribution map for one coil and the PI image are related to the same subject while differing in acquisition parameters.

According to Modification 1-2, a derived model is generated from a trained model based on a sensitivity distribution map for one coil acquired through a calibration scan in the parallel imaging, and a PI image acquired through an under-sampled scan is applied to the derived model so as to generate a noise-reduced PI image. As such, using the sensitivity distribution map acquired through the calibration scan conducted prior to the under-sampled scan, the derived model can be generated from the machine learning model intended for the PI image application. In other words, according to Modification 1-2, an online training process can be performed exclusively for one parallel imaging. Accordingly, the inference capability of the machine learning model for PI images can be improved while steady performance is guaranteed.

Modification 1-3

The foregoing examples have assumed that the medical data for training and the medical data for inference are acquired by different scanning operations. However, the embodiment is not limited to such configurations. Modification 1-3 will assume that the processing circuitry 11 obtains the medical data for training and the medical data for inference sequentially from one scanning operation. The scanning operations according to Modification 1-3 comply with, as a non-limiting example, parallel imaging according to a k-space method, such as generalized auto-calibrating partially parallel acquisition (GRAPPA) or auto-calibrating reconstruction for Cartesian imaging (ARC).

A brief description will be given of how the imaging is performed in the parallel imaging according to a k-space method. In the parallel imaging according to a k-space method, an MRI apparatus conducts a scan that complies with the parallel imaging according to a k-space method (hereinafter, a "k-space-PI scan") on a subject to acquire k-space data for each of multiple coils. Such a k-space-PI scan densely acquires data for one or more specific frequency regions in the k-space and sparsely acquires data for other frequency regions. In an exemplary configuration, the k-space-PI scan is a combination of a scan for intermittently acquiring data for k-space lines (under-sampled scan) and a scan for additionally acquiring data for the k-space line or lines in the central area of the k-space (additional scan). The under-sampled scan and the additional scan may be conducted one by one, or the additional scan may be incorporated in the middle of the under-sampled scan. Note that the specific frequency region is not limited to the k-space line or lines that cover the center of the k-space, but may be any k-space lines. Here, the k-space lines for which data acquisition is performed by the under-sampled scan may be called "acquisition lines", and the k-space lines for which data acquisition is not performed by the under-sampled scan and which then constitute missing portions may be called "incomplete acquisition lines". Also, among the incomplete acquisition lines, the lines for which further data acquisition is performed by the additional scan may be called "additional acquisition lines". The k-space data for such additional acquisition lines may be called ACS data. The ACS data is one example of additional data.

The MRI apparatus performs, for each of the multiple coils, the k-space-PI scan to acquire k-space data for multiple acquisition lines and k-space data for one or more additional acquisition lines. Then, for each of the coils, the MRI apparatus estimates k-space data that does not involve missing data based on the k-space data (ACS data) for the additional acquisition line or lines and the k-space data for the multiple acquisition lines, and generates an MR image by subjecting the estimated k-space data to reconstruction processing. The generated MR images do not include aliasing artifacts but include signal losses due to sensitivity unevenness among the coils. The MRI apparatus generates a single MR image (PI image) based on the multiple MR images corresponding to the respective coils. For example, the PI image here is generated by subjecting the multiple MR images corresponding to the respective coils to summation processing. As such, the PI image is an MR image with reduced signal losses due to sensitivity unevenness among the coils.

Figure 7:
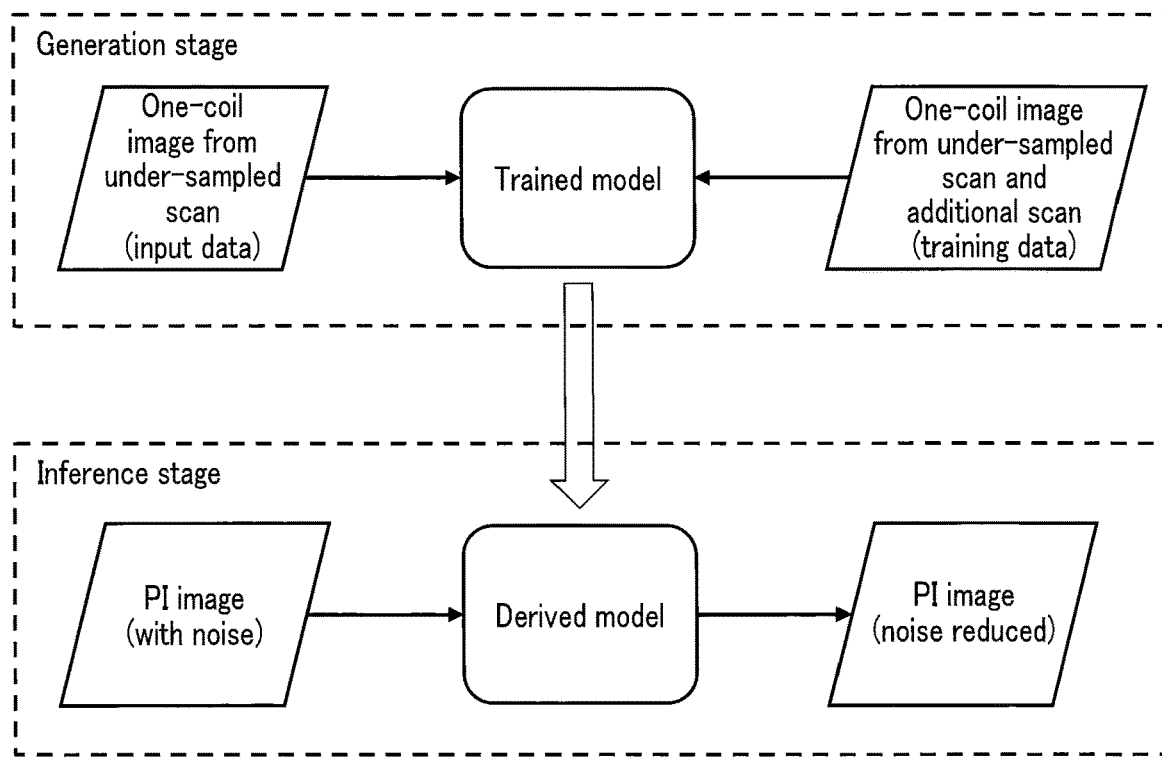
FIG. 7 is a diagram schematically showing an overview of an exemplary process performed by a medical data processing apparatus according to Modification 1-3.

FIG. 7 is a diagram schematically showing an overview of an exemplary process performed by the medical data processing apparatus 1 according to Modification 1-3. In the generation stage, the processing circuitry 11 obtains a one-coil image acquired through the under-sampled scan as a part of the k-space-PI scan, as shown in FIG. 7. The one-coil image from the under-sampled scan is obtained by reconstruction based on the k-space data set for the acquisition lines, which has been acquired by the under-sampled scan for one coil. Such a one-coil image from the under-sampled scan is one example of the first medical data. The processing circuitry 11 also obtains another one-coil image acquired through the under-sampled scan and also the additional scan of the k-space-PI scan. The one-coil image from both of the under-sampled scan and the additional scan is obtained by reconstruction based on the k-space data set for the acquisition lines, acquired by the under-sampled scan for one coil, and the k-space data (ACS data) for the additional acquisition line or lines. The one-coil image from the under-sampled scan and the additional scan has a higher image quality than the one-coil image from the under-sampled scan alone. The one-coil image from the under-sampled scan is set as input data, and the one-coil image from the under-sampled scan and the additional scan is set as training data, so that a derived model is generated from the trained model based on the input data and the training data.

In the inference stage, the processing circuitry 11 obtains a PI image acquired through the k-space-PI scan, as shown in FIG. 7. As described above, this PI image is obtained by reconstruction based on the multiple MR images corresponding to the respective coils and assumed to include noise. The processing circuitry 11 applies the PI image including noise to the derived model to generate a noise-reduced PI image. The noise-containing PI image is one example of the second medical data, and the noise-reduced PI image is one example of the third medical data. The one-coil image from the under-sampled scan and the PT image differ from each other in acquisition parameters such as image reconstruction methods. Thus, the one-coil image from the under-sampled scan and the PI image are related to the same subject while differing in acquisition parameters.

According to Modification 1-3, a derived model is generated from a trained model based on a one-coil image acquired from an under-sampled scan and another one-coil image acquired from the under-sampled scan and an additional scan, where the under-sampled scan and the additional scan constitute the k-space-PI scan complying with the parallel imaging. Then, a PI image acquired through the k-space-PI scan is applied to the derived model so as to generate a noise-reduced PI image. Accordingly, the use of medical data acquired from a single k-space-PI scan allows for generation of a derived model and inference with the derived model. That is, generation of a derived model and inference with the derived model can be done in the course of one scanning operation.

Modification 1-4

The foregoing examples that refer to FIG. 3 have assumed the instances of conducting a calibration scan and a single main scan in one examination. However, the embodiment is not limited to such instances, and may be applied to instances where three or more scanning operations are conducted in one examination. It is possible to employ various types of machine learning models for a scan image acquired through the third scan (namely, the second main scan) or a subsequent scan (in this modification, the image acquired through the second main scan is called a "second scan image"). In one example, the derived model that has been generated in step SA3 may be employed for the second scan image or a subsequent scan image. In other words, the second or subsequent scan image may be applied to the same derived model as that has been employed for the scan image acquired through the first main scan (in this modification, the image acquired through the first main scan is called a "first scan image"), that is, to the derived model generated based on the calibration data acquired through the calibration scan. In this case, the processing circuitry 11, upon finishing the use of the derived model for the scan image acquired through the last scan in the examination, saves a dump of the derived model and discards the derived model.

In another example, the processing circuitry 11 may update an existing derived model every time a scan image is generated, based on the generated scan image and in a cumulative manner. The processing circuitry 11 here cumulatively updates the derived model based on the first scan image and uses the updated derived model, as the latest derived model, for the second scan image. In this case, the processing circuitry 11, upon finishing the use of the latest derived model for the last scan image in the examination, saves a dump of the derived model and discards the derived model.

In yet another example, the processing circuitry 11 may generate a derived model from the trained model every time a scan image is generated, based on the previous scan image acquired through a preceding scan. The processing circuitry 11 here generates a derived model from the trained model based on the second scan image and uses the generated derived model for the third scan image. Instead, the processing circuitry 11 may generate a derived model from the trained model based on the first scan image and uses the generated derived model for the third scan image. In this case, the processing circuitry 11, upon finishing the use of the generated derived model, saves a dump of the derived model and discards the derived model.

According to Modification 1-4, improvement in the inference capability can be realized together with a guarantee of steady performance, also in the instances where three or more scanning operations are conducted in one examination.

Modification 1-5

The foregoing examples have assumed noise reduction processing, but the output objects are not required to always reflect the noise reduction processing. For example, the output objects may reflect a result of recognizing the region of interest (ROI) information for a next imaging subject. By changing one or more parameters by the online training process, ROI information can be selected or estimated with enhanced accuracy.

Example 2

Example 2 assumes that the medical data processing apparatus 1 is set at a work station. The medical data processing apparatus 1 according to Example 2 obtains medical data from an image storage apparatus, such as a PACS server, and analyzes the obtained medical data for various purposes. It will be assumed that the image storage apparatus here stores any given amount of medical data related to various subjects and collected by various medical image diagnostic apparatuses. While the medical data processing apparatus 1 according to Example 2 is capable of processing medical data collected by any medical image diagnostic apparatuses, the description will assume instances where the medical data processing apparatus 1 is dealing with medical data collected by an MRI apparatus, for the sake of explanation. Also, while processing contents of the machine learning models are not limited, this example assumes that the employed machine learning model is for analyzing medical images. The analysis processing is not particularly limited, but may include, for example, calculation of various indices for anatomical structures, image measurements, etc. Examples of the various indices include an apparent diffusion coefficient (ADC) in diffusion imaging, fractional anisotropy (FA), a cerebral blood volume (CBV) and a cerebral blood flow (CBF) in perfusion imaging, a mean transit time (MTT), and so on.

Figure 8:
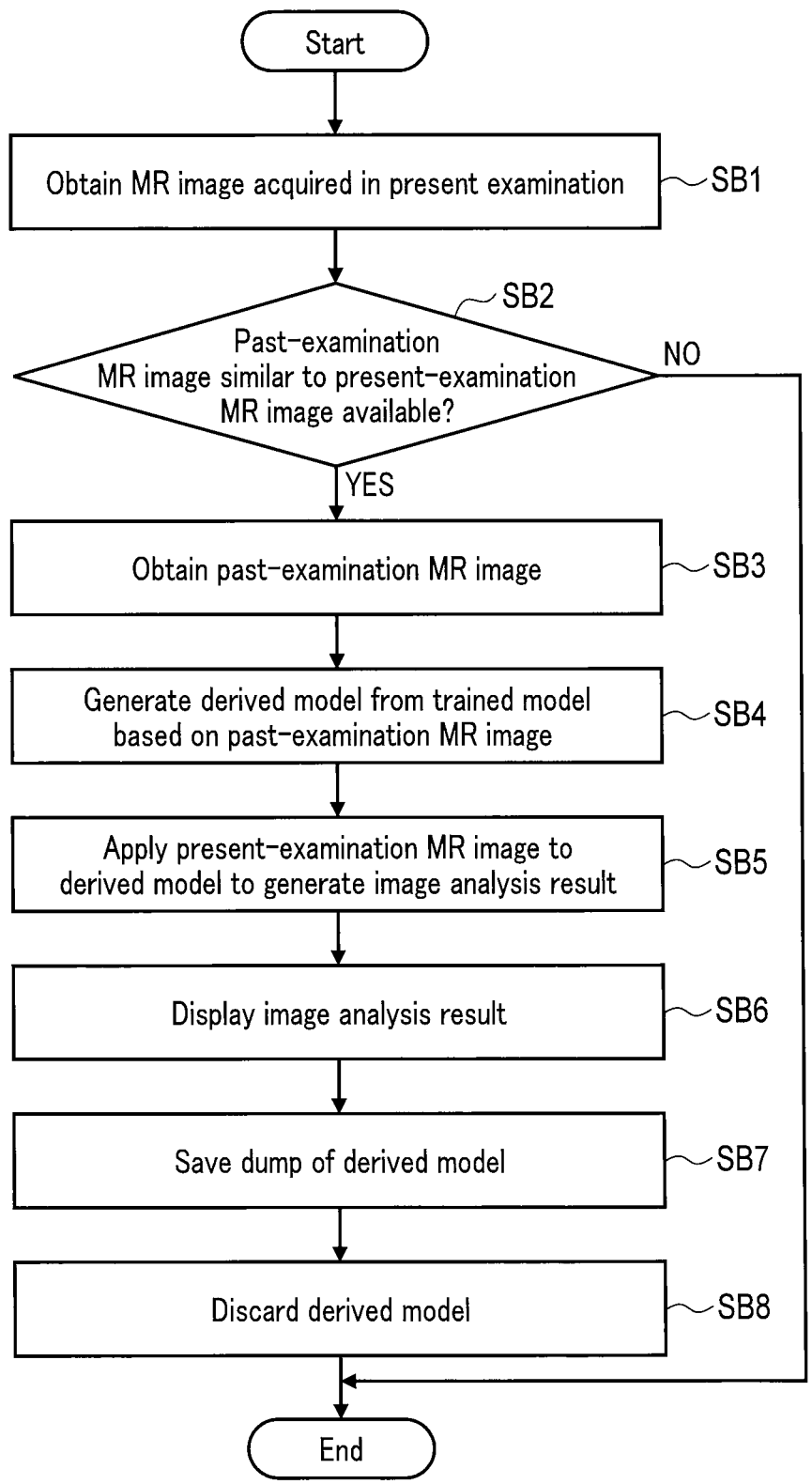
FIG. 8 is a diagram showing a typical flow of an exemplary process performed by a medical data processing apparatus according to Example 2.

FIG. 8 is a diagram showing a typical flow of an exemplary process performed by the medical data processing apparatus 1 according to Example 2. FIG. 9 is a diagram schematically showing an exemplary process performed by the medical data processing apparatus 1 according to Example 2.

As shown in FIGS. 8 and 9, the processing circuitry 11 in the generation stage implements the obtainment function 111 to obtain an MR image acquired in a present examination (step SB1). This present-examination MR image is an MR image that will be subjected to inference processing with a derived model. The term "present examination" indicates an examination to which the MR image to be subjected to the inference processing belongs. Also, examinations which have been performed prior to the present examination will be called "past examinations". In an exemplary configuration, the processing circuitry 11 obtains the present-examination MR image via the communication interface 12 from the image storage apparatus. The present-examination MR image is one example of the second medical data.

After step SB1, the processing circuitry 11 implements the generation function 112 to determine whether or not a past-examination MR image similar to the present-examination MR image is available (step SB2). More specifically, the processing circuitry 11 in step SB2 determines whether or not the image storage apparatus stores a past-examination MR image that is related to a same subject as the subject of the present-examination MR image and that is similar to the present-examination MR image. Virtually, such a similar past-examination MR image is an MR image showing a morphology substantially the same as the morphology of the anatomical structure showed on the present-examination MR image.

As a concrete processing, the processing circuitry 11 searches the image storage apparatus for a past-examination MR image similar to the present-examination MR image, according to search conditions. One of the search conditions may be an identifier of the subject of the present-examination MR image. This enables a determination that the subject of the present-examination MR image and the subject of one past-examination MR image are the same. As a search condition for securing the sameness in morphology of the anatomical structure, for example, a given number of days back from the date of the present examination may be set so that a range of the search for the similar past-examination MR image is limited to the number of past days corresponding to this number. The degree of temporal change in morphology of an anatomical structure depends on the age of a subject, and therefore, it is preferable that the number of days back be set according to the age of a subject. For example, when the subject is an adult, the number of days back may be suitably set to about two months, and when the subject is a child, the number of days back may be suitable set to about one month. Also, the setting of the search condition for securing the sameness in morphology of the anatomical structure may instead or additionally include a scan site, particulars of a scan sequence, and/or particulars of a contrast enhancement, which are the same as those of the present-examination MR image.

If it is determined in step SB2 that no similar past-examination MR image is available (step SB2: NO), the generation function 112 will not generate a derived model from the trained model. In this case, the processing circuitry 11 implements the inference function 113 to apply the present-examination MR image obtained in step SB1 to the trained model so that an analysis image is generated. The generated analysis image is presented through the display 13, etc.

On the other hand, if it is determined in step SB2 that a similar past-examination MR image is available (step SB2: YES), the processing circuitry 11 implements the obtainment function 111 to obtain the past-examination MR image determined to be similar (step SB3). More specifically, the processing circuitry 11 obtains the MR image that satisfies the search conditions set in step SB2, from the image storage apparatus. If there is more than one MR image that satisfies the search conditions, the processing circuitry 11 may obtain any one of such satisfactory MR images. For example, the obtained MR image here may be an MR image in a past examination that has the shortest temporal distance to the present examination, or an MR image with the highest similarity, or even an MR image that is selected according to other criteria. Note that, in this case of multiple MR images satisfying the search conditions, the processing circuitry 11 may also obtain two or more past-data MR images. As one example, supposing that multiple examinations have been conducted on the same subject every other month, the processing circuitry 11 may obtain MR images in the examinations performed within the past three months from the present examination (i.e., a past examination one month prior to the present examination, and a past examination two months prior to the present examination). The obtained past-examination MR image or images are one example of the first medical data. The present-examination MR image and each past-examination MR image differ from each other in examination date as one of the acquisition parameters.

After step SB3, the processing circuitry 11 implements the generation function 112 to generate, based on the past-examination MR image or images obtained in step SB3, a derived model from the trained model (step SB4). More specifically, the processing circuitry 11 generates the derived model by changing one or more adjustment parameters of the trained model based on the past-examination MR image or images. Example 2 assumes use of the trained model as a machine learning model trained to receive an MR image as an input and to output a result of image analysis based on the MR image. Such a trained model has been trained based on training data for various subjects so that the trained model is generalized to various subjects. In response to obtaining a single past-examination MR image, the processing circuitry 11 in step SB4 may generate the derived model from the trained model based on this single past-examination MR image in a manner similar to Example 1. In response to obtaining more than one past-examination MR image, the processing circuitry 11 may generate the derived model from the trained model based on these past-examination MR images. Since the derived model is generated from the trained model based on the MR image or images related to the inference target subject, the processing circuitry 11 suitably tailors the derived model to the subject while suppressing over-fitting, as compared to the trained model. Also, since the derived model is generated from the trained model based on an MR image or images similar to the present-examination MR image, the derived model is suitably tailored to the current morphology of the anatomical structure of the subject while suppressing over-fitting, as compared to the trained model.

After step SB4, the processing circuitry 11 implements the inference function 113 to apply the present-examination MR image obtained in step SB1 to the derived model generated in step SB4, so as to output a result of image analysis (step SB5). This image analysis result is one example of the third medical data. In step SB5, the present-examination MR image related to the inference target subject is not applied to the trained model generalized to various subjects but applied to the derived model tailored to the same specific inference target subject. Accordingly, inference processing that better fits the inference target subject can be performed, and the accuracy of image analysis will be enhanced.

After step SB5, the processing circuitry 11 implements the output control function 116 so that the image analysis result generated in step SB5 is presented (step SB6). In an exemplary implementation, the display 13 is caused to display an analysis image as the image analysis result. The processing circuitry 11 here may perform a control to display the image analysis result together with a message indicating the use of the derived model.

After step SB6, the processing circuitry 11 implements the discard function 114 so that a dump of the derived model is saved (step SB7). The processing in step SB7 is performed in a manner similar to step SA7 in FIG. 3.

After step SB7, the processing circuitry 11 also implements the discard function 114 to discard the derived model (step SB8). The processing in step SB8 is performed in a manner similar to step SA8 in FIG. 3.

The process performed by the medical data processing apparatus 1 according to Example 2 therefore comes to the end.

As described above, the processing circuitry 11 according to Example 2 generates a derived model from a trained model using first medical data acquired in a past examination for a subject, and applies second medical data acquired in a present examination for the same subject to the derived model. The processing circuitry 11 here generates the derived model based on the first medical data in a past examination that is similar to the second medical data in the present examination. Thus, the derived model is suitably tailored to the subject while suppressing over-fitting. Accordingly, the inference capability can be improved while steady performance is guaranteed.

The foregoing example does not intend any limitation, and various modifications are possible.

Modification 2-1

In the foregoing example, the present examination has been described as an examination to which the MR image subjected to the inference processing belongs, and the present examination has been assumed to be the most recent examination. However, the present examination is not limited to the most recent examination. There may be instances where the image storage apparatus stores an MR image acquired for the same subject and in an examination conducted after the present examination (hereinafter, such an examination having a later examination date than the present examination will be called a "later examination"). In such instances, the processing circuitry 11 in step SB2 may determine whether or not a later-examination MR image similar to the present-examination MR image is available.

Then the processing circuitry 11 in step SB3 may obtain the later-examination MR image, and in step SB4 generate a derived model from the trained model based on the obtained later-examination MR image.

Modification 2-2

The foregoing examples have assumed that a derived model is discarded once its use for one present-examination MR image is finished. According to this Modification 2-2, when analysis processing is expected for one MR image and also one or more other MR images acquired in the present examination, the processing circuitry 11 allows for the use of the same derived model for such one or more other MR images. This can reduce the load of repeatedly generating derived models. The processing circuitry 11 according to this modification may subject the derived model to the discard process upon receipt of an input of a discard instruction from a user, etc. via the input interface 14.

Example 3

The medical data processing apparatus 1 according to Example 3 will be described. The medical data processing apparatus 1 according to Example 3 may be mounted on a medical image diagnostic apparatus or set at a work station. Also, the machine learning models here are not limited to particular processing contents.

Figure 10:
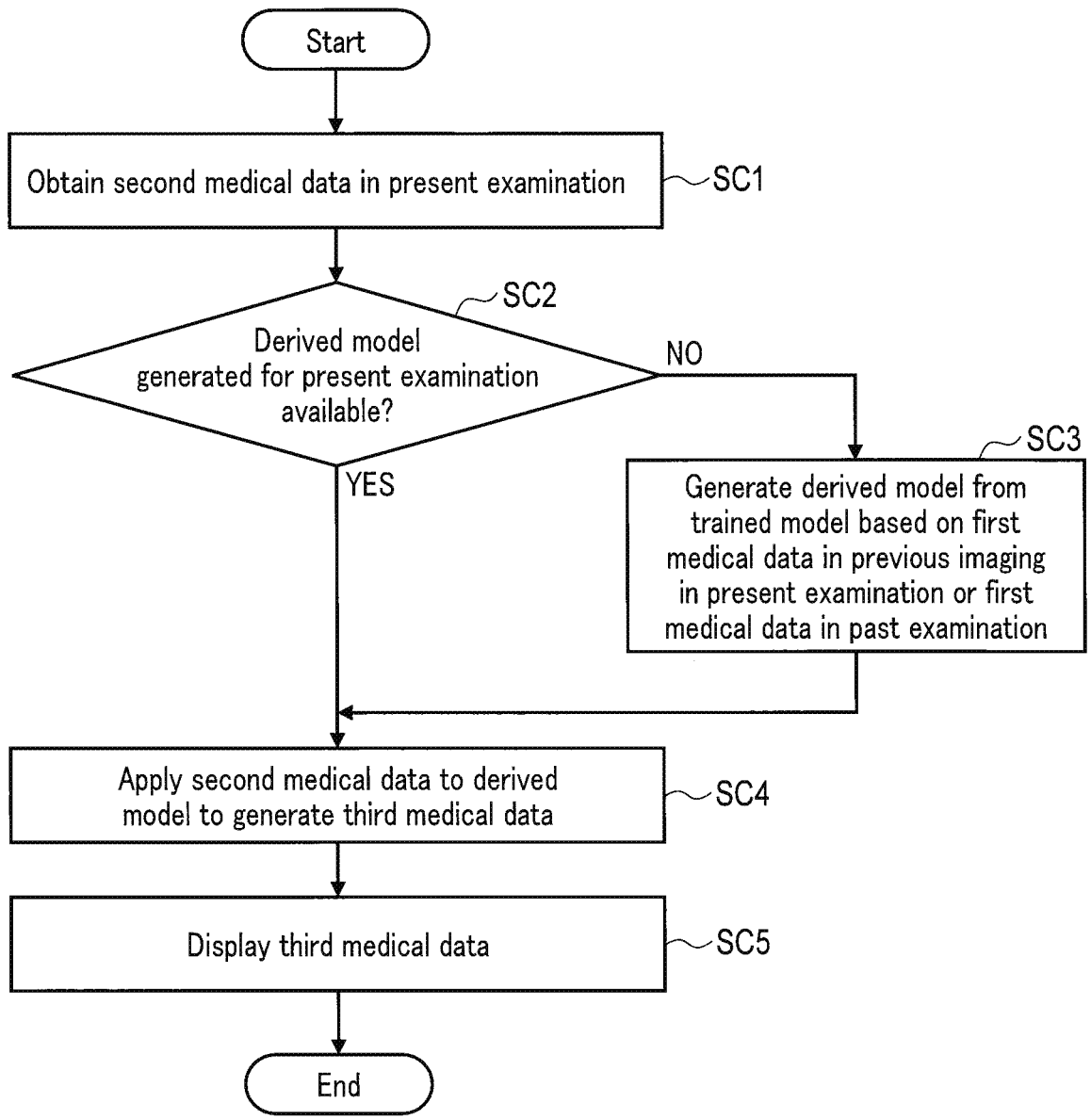
FIG. 10 is a diagram showing a typical flow of an exemplary process performed by a medical data processing apparatus according to Example 3.

FIG. 10 is a diagram showing a typical flow of an exemplary process performed by the medical data processing apparatus 1 according to Example 3. As shown in FIG. 10, the processing circuitry 11 in the generation stage implements the obtainment function 111 to obtain second medical data acquired in a present examination (step SC1). This present-examination second medical data is medical data that will be subjected to inference processing with a derived model.

After step SC1, the processing circuitry 11 implements the generation function 112 to determine whether or not there is a derived model generated for the present examination (step SC2). Similar to the foregoing examples, the derived model here is a machine learning model based on the trained model stored in the storage 15. In step SC2, the processing circuitry 11 makes this determination as to the presence or absence of the derived model by, for example, searching the storage regions including applicable memories such as a RAM adapted to temporarily retain calculation data produced by the processing circuitry 11, and the storage 15.

If it is determined in step SC2 that there is no generated derived model (step SC2: NO), the processing circuitry 11 implements the generation function 112 to generate a derived model from the trained model based on first medical data acquired in previous imaging in the present examination or first medical data acquired in a past examination (step SC3). More specifically, the processing circuitry 11 generates the derived model by changing one or more adjustment parameters of the trained model based on the first medical data in the previous imaging in the present examination or the first medical data in the past examination. The first medical data may be obtained in a manner similar to the foregoing examples.

If it is determined in step SC2 that the generated derived model is available (step SC2: YES), or if it is determined in step SC2 that the generated derived model is not available (step SC2: NO) and a derived model is then generated in step SC3, the processing circuitry 11 implements the inference function 113 to apply the second medical data obtained in step SC1 to the derived model so that third medical data is generated (step SC4). That is, in the former case of determining in step SC2 that the generated derived model is available (step SC2: YES), the processing circuitry 11 generates the third medical data by applying the second medical data obtained in step SC1 to the derived model that has been already generated for the present examination. In the latter case of determining in step SC2 that the generated derived model is not available (step SC2: NO) and generating a derived model in step SC3, the processing circuitry 11 generates the third medical data by applying the second medical data obtained in step SC1 to the derived model generated in step SC3.

In step SC5, the processing circuitry 11 implements the output control function 116 so that the third medical data generated in step SC4 is presented.

According to Example 3, the presence or absence of an already generated derived model for the present examination may be determined each time second medical data in the present examination is obtained. Then, if no generated derived model is available, a derived model is generated based on first medical data in previous imaging in the present examination or first medical data in a past examination, and the second medical data is applied to the derived model generated this time. If an already generated derived model is available, the second medical data is applied to this already generated derived model.

Example 4

Figure 11:
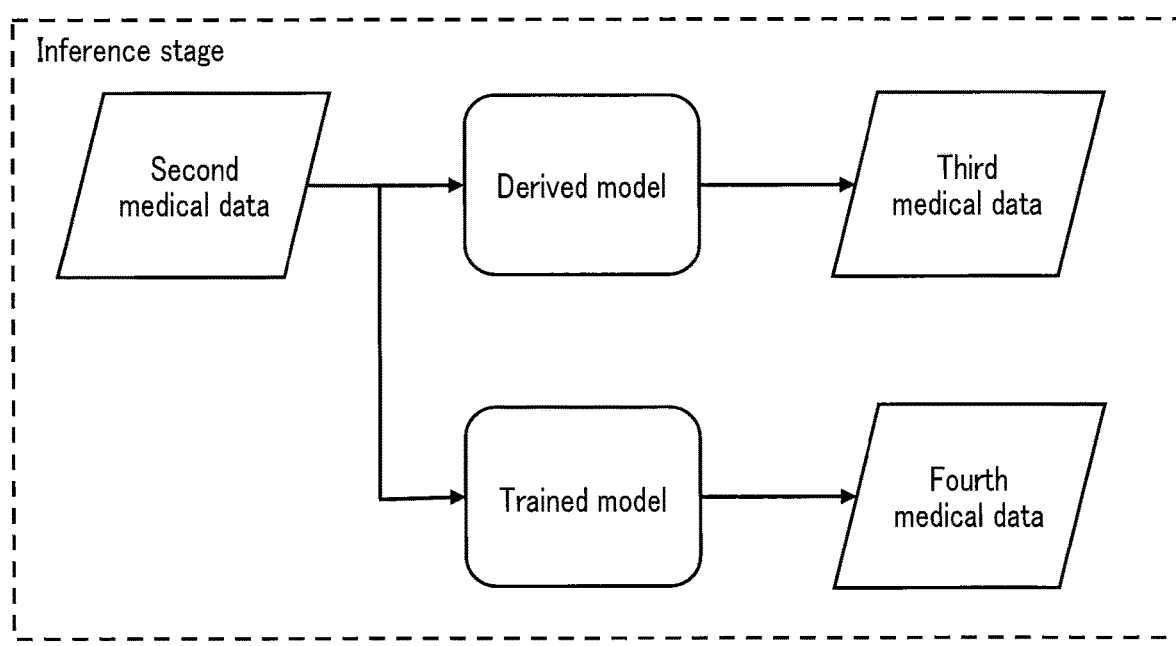
FIG. 11 is a diagram schematically showing an exemplary process performed by a medical data processing apparatus according to Example 4.

FIG. 11 is a diagram schematically showing an exemplary process performed by the medical data processing apparatus 1 according to Example 4. As shown in FIG. 11, the processing circuitry 11 in the inference stage may implement the inference function 113 to generate third medical data by applying second medical data to a derived model and generate fourth medical data by applying the second medical data to a trained model. The processing circuitry 11 implements the output control function 116 to cause the display 13 to display the third medical data and the fourth medical data. The third medical data and the fourth medical data may be presented side by side, or in a superimposed manner, for facilitating comparison. Also, the presentation of the third medical data may carry text or a symbol indicative of the use of the derived model for generating the third medical data, and the presentation of the fourth medical data may carry text or a symbol indicative of the use of the trained model for generating the fourth medical data.

According to Example 4, both the third medical data and the fourth medical data are generated respectively using a derived model suitably tailored to an intended subject and a trained model generalized to various subjects. Accordingly, in case the derived model is formed to have a degraded accuracy as compared to the accuracy of the trained model, it is possible to cover for the accuracy degradation.

According to at least one embodiment described above, improvement in the inference capability of a machine learning model and a guarantee of its performance can be realized at the same time.

The term "processor" used herein refers to, for example, a CPU or a GPU, or various types of circuitry, such as an application-specific integrated circuit (ASIC), a programmable logic device (e.g., a simple programmable logic device (SPLD), a complex programmable logic device (CPLD), or a field programmable gate array (FPGA)), and so on. The processor reads programs stored in the storage circuitry and executes them to realize the intended functions. The programs may be incorporated directly in circuits of the processor, instead of being stored in the storage circuitry. According to such architecture, the processor reads the programs incorporated in its circuits and executes them to realize the functions. As another option, functions corresponding to programs may be realized by a combination of logic circuits, instead of having the programs executed. Note that the embodiments herein do not limit each processor to a single circuitry-type processor. Multiple independent circuits may be combined and integrated as one processor to realize the intended functions. Furthermore, multiple components or features as given in FIG. 1 may be integrated as one processor to realize their respective functions.

While certain embodiments have been described, they have been presented by way of example only, and are not intended to limit the scope of the inventions. Indeed, the novel embodiments described herein may be embodied in a variety of other forms. Furthermore, various omissions, substitutions, and changes in the form of the embodiments may be made without departing from the spirit of the inventions. The accompanying claims and their equivalents are intended to cover such forms or modifications as would fall within the scope and spirit of the inventions.

The invention claimed is:

1. A medical data processing apparatus, comprising:
processing circuitry configured to
obtain first medical image data;
generate, based on the first medical image data, a derived model from a trained model;
obtain second medical image data for a same subject as a subject of the first medical image data and with a second acquisition parameter different from a first acquisition parameter of the first medical image data; and
apply the second medical image data to the derived model to generate third medical image data,
wherein the processing circuitry is further configured to store a dump of the derived model in a storage, and discard the derived model, after the derived model is used, and
the dump of the derived model includes an adjustment parameter of the derived model.

2. The medical data processing apparatus according to claim 1, wherein the processing circuitry is configured to obtain the first medical image data and the second medical image data, which are acquired in one examination, wherein the second medical image data is acquired through a second scan after a first scan for the first medical image data.

3. The medical data processing apparatus according to claim 1, wherein the processing circuitry is configured to:
obtain the first medical image data, which is acquired through a calibration scan, and
obtain the second medical image data, which is acquired through a main scan.

4. The medical data processing apparatus according to claim 1, wherein the processing circuitry is configured to:
obtain the first medical image data, which is acquired through a first main scan, and
obtain the second medical image data, which is acquired through a second main scan after the first main scan.

5. The medical data processing apparatus according to claim 1, wherein the processing circuitry is configured to:
obtain the first medical image data, which is acquired in a past examination for the subject, and
obtain the second medical image data, which is acquired in a present examination for the subject.

6. The medical data processing apparatus according to claim 1, wherein the processing circuitry is further configured to generate training data based on the first medical image data, and generate the derived model by changing a parameter of the trained model based on the first medical image data and the training data.

7. The medical data processing apparatus according to claim 6, wherein the processing circuitry is further configured to:
obtain additional medical data for a missing portion not included in the first medical image data, the additional medical data being acquired by an additional scan during parallel imaging, and
generate the training data based on the first medical image data and the obtained additional medical data.

8. The medical data processing apparatus according to claim 1, wherein the processing circuitry is further configured to:
set one or more of a plurality of parameters of the trained model as a fixed parameter or parameters, and a remaining one or more of the plurality of parameters as a change target parameter or parameters, and
change only the change target parameter or parameters.

9. The medical data processing apparatus according to claim 1, wherein the processing circuitry is configured to:
obtain the second medical image data, which is acquired in a present examination, and
obtain the first medical image data, which is acquired in an examination different from the present examination and represents a morphology of an anatomical structure equal to a morphology of an anatomical structure present in the second medical image data, and
wherein the processing circuitry is further configured to generate the derived model by changing a parameter of the trained model based on the first medical image data, and apply the second medical image data to the derived model to generate the third medical image data.

10. The medical data processing apparatus according to claim 1, wherein the first acquisition parameter and the second acquisition parameter includes any one of an examination date and time, a scan date and time, a slice position, a scan condition, and an image reconstructing technique.

11. The medical data processing apparatus according to claim 1, further comprising training the trained model through a training process with a plurality of training samples for a plurality of subjects, the trained model being assigned the adjustment parameter according to the training process.

12. The medical data processing apparatus according to claim 1, wherein the processing circuitry is further configured to generate the third medical image data by applying the second medical image data to the derived model, and generate fourth medical image data by applying the second medical image data to the trained model.

13. A medical data processing method, comprising:
obtaining first medical image data;
generating, based on the first medical image data, a derived model from a trained model;
obtaining second medical image data for a same subject as a subject of the first medical image data and with a second acquisition parameter different from a first acquisition parameter of the first medical image data; and
applying the second medical image data to the derived model to generate third medical image data,
wherein the method further comprises storing a dump of the derived model in a storage, and discard the derived model, after the derived model is used, and
the dump of the derived model includes an adjustment parameter of the derived model.

* * * * *